United States Patent [19]

Kuwana et al.

[11] Patent Number: 5,674,497
[45] Date of Patent: Oct. 7, 1997

[54] HAIR GROWTH PROMOTER COMPRISING EXTRACT OF MULBERRY ROOT BARK AND PERSIMMON AND/OR PAULOWNIA, OR EXTRACT OF PERSIMMON AND PAULOWNIA

[75] Inventors: Ryuichiro Kuwana, Kochi-ken; Atsunori Okada, Kagawa-ken; Masafumi Morioka, Kagawa-ken; Akemi Date, Kagawa-ken, all of Japan

[73] Assignee: Fuji Sangyo Co., Ltd., Marugame, Japan

[21] Appl. No.: 451,276

[22] Filed: May 30, 1995

[30] Foreign Application Priority Data

Jun. 1, 1994 [JP] Japan ................................ 6-140715

[51] Int. Cl.$^6$ ........................................... A61K 7/06
[52] U.S. Cl. ........................................... 424/195.1
[58] Field of Search ................................ 424/195.1

[56] References Cited

U.S. PATENT DOCUMENTS

Re. 33,993  7/1992  Grollier et al. ................. 424/195.1

FOREIGN PATENT DOCUMENTS

| 54-72576 | 6/1979 | Japan . |
|---|---|---|
| 56-153867 | 4/1983 | Japan . |
| 59-109167 | 5/1984 | Japan . |
| 60-182773 | 8/1985 | Japan . |
| 31371 | 11/1990 | Japan . |
| 0381517 | 3/1991 | Japan . |
| 03297579 | 5/1993 | Japan . |
| 355476 | 7/1994 | Japan . |

*Primary Examiner*—Peter F. Kulkosky
*Attorney, Agent, or Firm*—Frishauf, Holtz, Goodman, Langer & Chick, P.C.

[57] ABSTRACT

The hair growth promoter of the present invention contains extracts from two or three of mulberry bark (mulberry root bark of Morus bombycis Koidzumi and Morus alba Linne or a plant of the same genus as that of them), leaves of persimmon (Diospyros Kaki Thunb) and leaves of paulownia (Paulowinia tomantosa Steud. or plants of the same genus as that thereof) as the active ingredients for restoring or growing hair.

The hair growth promoter of the present invention has an effect of accelerating the proliferation of the human hair follicle cells which constitute the human hair follicle and which form the hair and also an effect of accelerating the hair growth in mice. When the hair growth promoter is applied to the human beings, excellent effects of preventing the hair from falling out and accelerating the hair growth are obtained. Thus, the hair growth promoter of the present invention is effectively usable for the treatment or prevention of an alopecia such as premature alopecia or alopecia diffuse.

18 Claims, No Drawings

HAIR GROWTH PROMOTER COMPRISING EXTRACT OF MULBERRY ROOT BARK AND PERSIMMON AND/OR PAULOWNIA, OR EXTRACT OF PERSIMMON AND PAULOWNIA

FIELD OF THE INVENTION

The present invention relates to a new hair growth promoter useful for medical treatment or the like. In particular, the present invention relates to a hair growth promoter to be applied to the scalp for the treatment of an alopecia such as premature alopecia (male pattern baldness) or alopecia diffuse, for prevention of the hair from falling out or for accelerating the hair growth.

BACKGROUND OF THE INVENTION

Numerous hair tonics mainly comprising a mixture of herb extracts have been known hitherto.

However, the hair growing effect of them is yet far from satisfaction.

Although the age of the premature alopicia patients is now getting younger, and the number of the patients is increasing, no medicine having an exact effect has been developed yet. Various hair dressings and hair tonics have been used just to ease the patient's mind.

In addition, falling out of hair and alopecia of woman are also increasing recently supposedly because female working members of society are now remarkably increasing and also for various complicated reasons. However, no remarkable measures are taken to deal with the situation. Although various hair tonics have been developed and put on the market, the effects of them are yet unsatisfactory according to the objective evaluation.

Further, even when the results of the tests are described to be "remarkably improved" in many literatures, the criteria of the tests are yet uncertain. There is no report at all that the growth of "lanugo hair, veilus hair or terminal hair" was recognized.

The alopecia is usually classified into various types depending on the cause and symptoms thereof. Main types are premature alopecia, alopecia diffuse and alopecia totalis. Among them, alopecia totalis is transient and it can be completely recovered by a dermatological treatment in many cases, but the former two types of alopecia are difficulty to treat. The premature alopecia is strongly influenced by genetic effects, and it is said that the premature alopecia is caused by a male sex hormone or peripheral circulatory failure. It is also said that the premature alopecia is influenced by abnormal sebiferous, excess dandruff formation and undernutrition. It is said that the alopecia diffuse of women are caused by incomplete blood circulation into the hair follicles and excess care of hair such as excess shampoo and brushing.

The following ingredients are contained in the ordinary hair growth promoters for the above-described reasons: ingredients for improving the periphery circulation such as Japanese chiretta (Swertia japonica Makino) extract, garlic extract, carpronium chloride, ginger tincture, cayenne pepper tincture and vitamin E; ingredients for the treatment of abnormal sebiferous such as pyridoxine and derivatives thereof; ingredients for the treatment of excess dandruff formation such as isopropylphenol, hinokitiol and salicylic acid; anti-inflammatory agent such as glycyrrhetinic acid, hinokitiol and diphenhydramine chloride; and cell-activating agents such as light-sensitive element #301, hinokitiol, placenta extract and pentadecanoic acid glyceride.

However, although these ingredients are effective to some extent in improving each of the symptoms, they are yet ineffective in inhibiting the alopecia. Further, a female sex hormone antagonistic to male sex hormone is given to a premature alopecia patient, since the male sex hormone is concerned with the alopecia of this type. However, the intended effect thereof cannot be obtained, since an effective dose of the female sex hormone cannot be administered to the patient because of side effects.

Thus, no drastic method for the treatment of the premature alopecia or alopecia diffuse has been developed. It is supposed, however, that a substance capable of accelerating the hair follicle cell proliferation or a substance capable of converting a hair in a resting stage into a hair in a growing stage is usable as an effective hair growth promoter, since the alopecia is caused by the inhibition of the hair follicle cells from proliferation to convert the hair in the growing stage (i.e. the stage in which the hair grows; at least 90% of normal human head hair being in the growing stage) into the resting stage (i.e. the stage in which the hair no longer grows and it falls out; about 10% of normal human head hair being in this stage).

SUMMARY OF THE INVENTION

The object of the present invention is to provide a hair growth promoter capable of constituting the human hair follicle and having an effect of accelerating the proliferation of human hair follicle cells for forming the hair and an effect of accelerating the hair growth of mice, the hair growth promoter exhibiting excellent effect of curing and preventing alopecia and accelerating the hair growth upon application to the human scalp.

DETAILED DESCRIPTION OF THE INVENTION

The inventors made investigations for a long period of time for the purpose of developing a hair restoring or growing agent capable of proliferating hair follicle cells and exhibiting the hair restoring or growing effect in the actual use or, in other words, capable of growing "lanugo hair, veilus hair or terminal hair" to such an extent that the growth can be confirmed.

As a result, the inventors have found that a mixture of extracts from two or three of mulberry bark, persimmon leaves and paulownia leaves has an excellent effect of restoring or growing hair in cases of premature and female alopecia.

The present invention has been completed on the basis of this finding.

Namely, the present invention provides (1) a hair growth promoter characterized by containing, as an active ingredient, an extract obtained by extraction from a mixture of mulberry bark (mulberry root bark of Morus bombycis Koidzumi and Morus alba Linne or a plant of the same genus as that of them) and leaves of persimmon (Diospyros Kaki Thunb) with an extracting solvent.

The present invention provides (2) a hair growth promoter characterized by containing, as an active ingredient, a mixture of an extract obtained by extraction from the mulberry bark with an extracting solvent and an extract obtained by extraction from leaves of persimmon with an extracting solvent.

The present invention provides (3) a hair growth promoter characterized by containing, as an active ingredient, a mixture of an extract obtained by extraction from a mixture of the mulberry bark and persimmon leaves with an extracting solvent and an extract obtained by extraction from leaves of paulownia (Paulowinia tomantosa Steud. or plants of the same genus as that thereof) with an extracting solvent.

The present invention provides (4) a hair growth promoter characterized by containing, as an active ingredient, a mixture of an extract obtained by extraction from the mulberry bark with an extracting solvent, an extract obtained by extraction from persimmon leaves with an extracting solvent and an extract obtained by extraction from paulownia leaves with an extracting solvent.

The present invention provides (5) a hair growth promoter characterized by containing, as an active ingredient, a mixture of an extract obtained by extraction from the mulberry bark with an extracting solvent and an extract obtained by extraction from paulownia leaves with an extracting solvent.

The present invention provides (6) a hair growth promoter characterized by containing, as an active ingredient, a mixture of an extract obtained by extraction from persimmon leaves with an extracting solvent and an extract obtained by extraction from paulownia leaves with an extracting solvent.

The mulberry bark used herein is an original name of "Soukon hakuhi" described in Shinnou-Honzoukyo, which is a bark of a root of Morus alba Linne or a plant of the same genus as that thereof. This is a crude drug included in the 12th Revision of Japanese Pharmacopeia. The origin is Morus bombycis Koidzumi which grows naturally in fields and mountains in Japan and which is also widely cultivated in not only Japan but also Korea, Sakhalin and the south Kuriles. Both of these two kinds of mulberries are used in the present invention.

The term "persimmon leaves" herein indicates leaves of trees of Diospyros Linn, Ebenareae. These are leaves of persimmons (Diospyros Kaki Thunb) which are tall deciduous trees usually caltivated in gardens and orchards. It has been known that persimmon leave tea is taken for the purpose of preventing high blood pressure and arteriosclerosis or strengthening a weak constitution, taking advantage of the effects of vitamins A, B and C contained therein. However, it has not yet been proved that the persimmon leaves have the hair growing effect in the basic investigations or clinical studies of persimmon leave extract.

The term "paulownia leaves" herein indicates leaves of paulownia (Paulownia tomentosa Steud.) (Paulownia, Scrophulariaceae) or a plant of the same genus as that thereof. Although the paulownia leaves containing eleostearic acid and ursolic acid have been used as a folk medicine for the treatment of skin diseases, they have been used not so often, since their effect is not so strong. It has been unknown hitherto that the paulownia leaves have the hair growing effect.

The hair growth promoter of the present invention contains extracts from two or three of mulberry bark, persimmon leaves and paulownia leaves as the active ingredients for restoring or growing hair.

These extracts have various embodiments.

They include (1) an extract obtained by extraction from a mixture of mulberry bark and persimmon leaves with an extracting solvent, (2) a mixture of an extract obtained by extraction from mulberry bark with an extracting solvent and an extract obtained by extraction from persimmon leaves with an extracting solvent, (3) a mixture of an extract obtained by extraction from a mixture of the mulberry bark and persimmon leaves with an extracting solvent and an extract obtained by extraction from paulownia leaves with an extracting solvent, (4) a mixture of an extract obtained by extraction from the mulberry bark with an extracting solvent, an extract obtained by extraction from persimmon leaves with an extracting solvent and an extract obtained by extraction from paulownia leaves with an extracting solvent, (5) a mixture of an extract obtained by extraction from the mulberry bark with an extracting solvent and an extract obtained by extraction from paulownia leaves with an extracting solvent and (6) a mixture of an extract obtained by extraction from persimmon leaves with an extracting solvent and an extract obtained by extraction from paulownia leaves with an extracting solvent.

The composition of each of the extracts from mulberry bark, persimmon leaves and paulownia leaves has not been fully elucidated yet. The extracts can be obtained by methods described below.

Since the paulownia leaves are different from the mulberry bark and persimmon leaves in the extracting solvent and extraction method, the extraction from the paulownia leaves is conducted separately as described above.

The mulberry bark, persimmon leaves and paulownia leaves are used as they are or, if necessary, after pulverizing or cutting them into a suitable size.

Either or a mixture of both of the mulberry bark and persimmon leaves, which are suitably pulverized or cut into small pieces, in a suitable ratio is treated with an extracting solvent selected from among hydrophilic organic solvents, hydrous organic solvents and oleophilic organic solvent.

Examples of the hydrophilic organic solvents include methanol, ethanol, acetone, dioxane, tetrahydrofuran, isopropanol and n-propanol. Among them, methanol, ethanol and acetone are particularly preferred.

Examples of the hydrous organic solvents include hydrous methanol, hydrous ethanol and hydrous acetone.

Examples of the lipophilic organic solvents include n-butanol, n-hexanol, n-amyl alcohol, ethyl acetate, propyl acetate, butyl acetate, methylene chloride, chloroform, carbon tetrachloride, benzene, toluene, xylene, diethyl ether, petroleum ether and n-hexane. Among them, particularly preferred are n-hexane, ethyl acetate, diethyl ether, benzene, toluene and xylene.

Also paulownia leaves are used as they are or, if necessary, after pulverizing or cutting them into a suitable size.

The paulownia leaves as they are or suitably pulverized or cut are treated with hot water or a hydrous organic solvent as the extracting agent to obtain the extract.

In the extraction from one of mulberry bark and persimmon leaves or a mixture of them in a suitable ratio with the hydrous organic solvent as the extracting solvent, the relative amount of the organic solvent in the hydrous organic solvent is at least 30%, preferably at least 70%.

In the extraction from paulownia leaves with the hydrous organic solvent as the extracting solvent, the relative amount of the organic solvent in the hydrous organic solvent is at most 50%, preferably at most 30%.

In the extraction, about 5 to 20 parts by weight, preferably 10 to 15 parts by weight, of the above-described extracting solvent is added to 1 part by weight of the mulberry bark, persimmon leaves or paulownia leaves or a mixture of them, and the resultant mixture is heated under reflux or is left to stand at ambient temperature for at least 3 days, preferably at least 1 week.

In the extraction from the paulownia leaves with hot water, 1 part by weight of the leaves are immersed in about 5 to 20 parts by weight, preferably 10 to 15 parts by weight, of hot water (having a temperature of 80° to 100°, preferably 90° to 100° C.) for 30 min to 4 h, preferably for 1 to 2 h.

The extract solution thus obtained is filtered and then concentrated to remove the solvent and thereby to obtain the extract.

The hair growth promoter of the present invention contains a mixture of two or three of the extracts thus obtained as the components for accelerating the restoring or growing of hair, i.e. active ingredients.

Since the extracts from mulberry bark and persimmon leaves can be obtained with the same extracting solvent by the same extraction method, an extract obtained from a mixture of mulberry bark and persimmon leaves can also be used.

As for the amount of the components for accelerating the restoring or growing of hair, the amount of the mulberry bark extract is usually 0.001 to 20% by weight (in terms of the solid), preferably 0.1 to 5% by weight, on the basis of the whole hair growth promoter; that of the persimmon leaf extract is usually 0.001 to 20% by weight (in terms of the solid), preferably 0.05 to 3% by weight, on the basis of the whole hair growth promoter; and that of the paulownia leaf extract is usually 0.001 to 20% by weight (in terms of the solid), preferably 0.1 to 10% by weight, on the basis of the whole hair growth promoter.

The components for accelerating the restoring or growing of hair obtained as described above are dissolved in an oil, fat, cream or the like such as hydrous ethanol or camellia oil to obtain the hair growth promoter in a form which will be described below.

Other starting substances used for forming the hair growth promoter of the present invention are those usually contained in hair growth promoters, such as hydrocarbons, waxes, oils, fats, esters, higher fatty acids, higher alcohols, surfactants, flavors, colorants, antiseptics, antioxidants, ultraviolet screening agents, alcohols and pH regulators; and pharmaceutical hair-growing components such as agents for dissolving the epidermal keratin, disinfectants, anti-inflammatory agents, antiseborrheics, blood circulation improvers, cell activating agents, local irritating agents and antipruritic agents. The hair growth promoter is prepared by suitably selecting the starting substances.

The hair growth promoter of the present invention can be in various forms such as liquid, cream, ointment, gel and aerosol forms. They include hair cream, hair tonic, hair lotion, hair treatment, hair liquid, hair mousse, hair gel, hair spray, hair shampoo and hair rinse.

The following Examples will further illustrate the present invention, which by no means limit the scope of the invention.

PRODUCTION EXAMPLE 1

200 g of mulberry bark was immersed in 2 l of ethyl acetate at room temperature for 7 days to extract components soluble in ethyl alcohol. Thus, 1.8 l of the extract solution was obtained. Then ethyl acetate was distilled off from the extract solution, and the residue was further dried to obtain 7.5 g of a light brown mulberry bark extract.

PRODUCTION EXAMPLE 2

200 g of persimmon leaves were immersed in 2 l of 70% ethanol at room temperature for 7 days to extract components soluble in 70% ethanol. Thus, 1.8 l of the extract solution was obtained. Then 70% ethanol was distilled off from the extract solution, and the residue was further dried to obtain 17.0 g of a dark green persimmon leaf extract.

PRODUCTION EXAMPLE 3

A mixture of 100 g of mulberry bark and 100 g of persimmon leaves was immersed in 2 l of 80% methanol at room temperature for 7 days to extract components soluble in 80% ethanol. Thus, 1.8 l of the extract solution was obtained. Then 80% methanol was distilled off from the extract solution, and the residue was further dried to obtain 13.5 g of a dark green extract from the mixture of mulberry bark and persimmon leaves.

PRODUCTION EXAMPLE 4

200 g of paulownia leaves were added to 2 l of water, and the resultant mixture was boiled for 1 h to extract components soluble in the boiling water. Thus, 1.7 l of the extract solution was obtained. Then water was distilled off from the extract solution, and the residue was further dried to obtain 31.6 g of a dark brown extract from the paulownia leaves.

PRODUCTION EXAMPLE 5

200 g of mulberry bark was immersed in 2 l of acetone at room temperature for 7 days to extract components soluble in acetone. Thus, 1.8 l of the extract solution was obtained. Then acetone was distilled off from the extract solution, and the residue was further dried to obtain 8.3 g of a light brown mulberry bark extract.

PRODUCTION EXAMPLE 6

200 g of paulownia leaves were added to 2 l of 30% ethanol, and the resultant mixture was left to stand at ambient temperature for one week and then filtered. The filtrate was concentrated to distill off 30% ethanol, and the residue was further dried to obtain 28.0 g of a dark green extract from the paulownia leaves.

COMPARATIVE EXAMPLE 1

5.0 g of the yellowish brown extract obtained in Production Example 1 was dissolved in 1 l of 70% ethanol. The solution was left to stand in a cold room for 3 days and then filtered to obtain the hair growth promoter.

The hair growth promoter (test drug) thus obtained was tested to find whether it was effective in accelerating the division and proliferation of the human hair follicle cells by a test of acceleration of proliferation of human hair follicle cells, wherein the hair follicles were those of drawn out hairs.

[Test of acceleration of proliferation of human hair follicle cells by using follicles of drawn out hairs]

The lower ⅓ of each of the hair follicles in the growing stage which were drawn out of the human scalp was treated with trypsin to obtain a cell suspension. About 30,000 cells of the suspension were applied to a tissue culture dish having a diameter of 35 mm to which IV type collagen had been applied. The culture was conducted at a temperature of 37° C. in an atmosphere comprising 5% of carbon dioxide and 95% of air. The culture medium used was KGM medium (a product of Kurabo Industries Ltd.). After the proliferation of the follicle cells, they were peeled off with trypsin to obtain a cell suspension.

About 20,000 cells of the suspension were applied to a different tissue culture dish having a diameter of 35 mm to which IV type collagen had been applied to conduct the culture. 24 h after the initiation of the culture, the medium was replaced with a medium containing 0.001% of the hair growth promoter(test drug). The medium was renewed at intervals of 24 h, and the culture was conducted for 144 h.

The proliferated cells were peeled off with trypsin and counted with a hemocytometer. The number of the cells was given in terms of a relative value to that (100%) of a control.

The number of the cells obtained after the culture for 144 h is given in Table 1. 70% ethanol was used as the control.

COMPARATIVE EXAMPLE 2

The same procedure as that of Comparative Example 1 was repeated except that 5.0 g of the light brown extract obtained in Production Example 1 was replaced with 5.0 g of the dark green extract obtained in Production Example 2 to obtain the hair growth promoter, and the number of the cells was counted after the culture for 144 1 h. The results are given in Table 1.

EXAMPLE 1

The same procedure as that of Comparative Example 1 was repeated except that 5.0 g of the light brown extract obtained in Production Example 1 was replaced with 5.0 g of the dark green extract obtained in Production Example 3 to obtain the hair growth promoter, and the number of the cells was counted after the culture for 144 h. The results are given in Table 1.

EXAMPLE 2

The same procedure as that of Comparative Example 1 was repeated except that 5.0 g of the light brown extract obtained in Production Comparative Example 1 was replaced with 2.5 g of the light brown extract obtained in Production Example 1 and 2.5 g of the dark green extract obtained in Production Example 2 to obtain the hair growth promoter, and the number of the cells was counted after the culture for 144 h. The results are given in Table 1.

COMPARATIVE EXAMPLE 3

The same procedure as that of Comparative Example 1 was repeated except that 5.0 g of the light brown extract obtained in Production Example 1 was replaced with 5.0 g of the dark brown extract obtained in Production Example 4 and that 70% ethanol was replaced with 40% ethanol to obtain the hair growth promoter, and the number of the cells was counted after the culture for 144 h. The results are given in Table 1.

EXAMPLE 3

The same procedure as that of Comparative Example 1 was repeated except that a hair growth promoter obtained by dissolving 2.5 g of the light brown extract obtained in Production Example 1, 2.5 g of the dark brown extract obtained in Production Example 4 and 10 g of polyoxyethylene-hardened castor oil in 1 l of 40% ethanol, leaving the solution to stand in a dark room for 3 days and filtering the solution was used, and the number of the cells was counted after the culture for 144 h. The results are given in Table 1.

EXAMPLE 4

The same procedure as that of Comparative Example 1 was repeated except that a hair growth promoter obtained by dissolving 2.5 g of the dark green extract obtained in Production Example 2, 2.5 g of the dark brown extract obtained in Production Example 4 and 10 g of polyoxyethylene-hardened castor oil in 1 l of 40% ethanol, leaving the solution to stand in a dark room for 3 days and filtering the solution was used, and the number of the cells was counted after the culture for 144 h. The results are given in Table 1.

EXAMPLE 5

The same procedure as that of Comparative Example 1 was repeated except that a hair growth promoter obtained by dissolving 1.5 g of the light brown extract obtained in Production Example 1, 2.0 g of the dark green extract obtained in Production Example 2, 1.5 g of the dark brown extract obtained in Production Example 4 and 10 g of polyoxyethylene-hardened castor oil in 1 l of 40% ethanol, leaving the solution to stand in a dark room for 3 days and filtering the solution was used, and the number of the cells was counted after the culture for 144h. The results are given in Table 1.

TABLE 1

| | | Number of cells after culture for 144 h. |
|---|---|---|
| Control | 70 % ethanol | 100% |
| Comparative Example 1 | Mulberry bark extract (obtained in Production Ex. 1) | 121% |
| Comparative Example 2 | Persimmon leaf extract (obtained in Production Ex. 2) | 146% |
| Example 1 | Extract from mixture of mulberry bark and persimmon leaves (obtained in Production Ex. 3) | 188% |
| Example 2 | Mulberry bark extract (obtained in Production Ex. 1) + persimmon leaf extract (obtained in Production Ex. 2) | 176% |
| Comparative Example 3 | Paulownia leaf extract (obtained in Production Ex. 4) | 135% |
| Example 3 | Mulberry bark extract (obtained in Production Ex. 1) + paulownia leaf extract (obtained in Production Ex. 4) | 165% |
| Example 4 | Persimmon leaf extract (obtained in Production Ex. 2) + paulownia leaf extract (obtained in Production Ex. 4) | 181% |
| Example 5 | Mulberry bark extract (obtained in Production Ex. 1) + persimmon leaf extract (obtained in Production Ex. 2) + paulownia leaf extract (obtained in Production Ex. 4) | 197% |

It is apparent from the results given in Table 1 that the hair growth promoter of the present invention has a more remarkable effect of accelerating the proliferation of the human hair follicle cells than that of 70% ethanol used as the control in the test. It is also apparent that the hair growth promoters comprising two or more extracts are more effective in accelerating the proliferation of the human hair follicle cells than the hair growth promoters comprising only one extract.

EXPERIMENT EXAMPLE 1

[Hair regrowing rate test with C3H/HeSlc mice]

The hair regrowing rate tests were conducted as described below with reference to publications of Ogawa et al.

In the test, hair on the back of each C3H/HeSlc mouse (7 week old) was clipped. Each group consisted of five mice in the resting stage of hair growth.

10 samples (the hair growth promoters produced in Comparative Examples 1 to 3 and Examples 1 to 5, a furozin solution and 70% ethanol solution) in total were applied to the mice in a dose of 0.1 ml/animal/8 cm²/day) once a day, and the hair growing state was observed for 4 weeks. The rate of the area of a part in which hair was regrown in the clipped part was determined, and the hair regrowing rate was calculated according to the formula given below. The results are given in Table 2.

Hair regrowing rate (%)=[(area of hair growing part)/(area of clipped part)]×100

It is recognized from Table 2 that large differences were recognized among the samples after the application for two weeks. The differences became wider with time to prove that the hair growing-accelerating effect of the hair growth promoter of the present invention on mice is far more excellent than that of the furozin solution or 70% ethanol solution. It was also proved that the mixture of three extracts from mulberry bark, persimmon leaves and paulownia leaves has a particularly excellent effect.

stage of advance in each group would be equal. In the clinical test, 10 samples (the hair growth promoters produced in Comparative Examples 1 to 3, and Examples 1 to 5, a furozin solution and 70% ethanol solution) in total were applied to the patients to evaluate the effects of them. Each sample was externally applied to the scalp twice a day for four months. After four months, the hair growing state was examined. The degree of the improvement was evaluated and classified into the following four ranks to obtain the results given in Table 3.

[Criteria]

Remarkable improvement: Fresh and terminal hair was recognized.

Improvement: Fresh and veilus hair was recognized.

Slight improvement: Reduction in falling out of hair was recognized.

Unchanged: No change was recognized at all.

TABLE 2

(Change in hair regrowing rate with time)

| | Hair regrowing rate (%) | | | | | |
|---|---|---|---|---|---|---|
| | 6 days | 7 days | 10 days | 12 days | 14 days | 16 days |
| Comparative Example 1 | 0.0 ± 0.0 | 4.0 ± 1.5 | 7.3 ± 4.3 | 11.4 ± 1.9 | 16.2 ± 4.1 | 28.5 ± 3.7 |
| Comparative Example 2 | 0.0 ± 0.0 | 0.2 ± 0.1 | 5.5 ± 2.5 | 8.2 ± 4.2 | 12.4 ± 3.7 | 15.2 ± 5.2 |
| Example 1 | 0.0 ± 0.0 | 10.1 ± 2.5 | 15.5 ± 3.5 | 20.2 ± 3.5 | 28.4 ± 5.1 | 35.2 ± 4.2 |
| Example 2 | 0.0 ± 0.0 | 9.8 ± 1.8 | 14.6 ± 3.2 | 21.6 ± 4.3 | 27.4 ± 5.1 | 33.6 ± 4.8 |
| Comparative Example 3 | 0.0 ± 0.0 | 0.5 ± 0.5 | 5.6 ± 2.3 | 8.2 ± 3.7 | 10.9 ± 3.5 | 16.4 ± 6.3 |
| Example 3 | 0.0 ± 0.0 | 10.6 ± 2.3 | 16.1 ± 3.9 | 21.1 ± 4.0 | 28.6 ± 6.7 | 37.2 ± 5.0 |
| Example 4 | 0.0 ± 0.0 | 8.7 ± 0.9 | 14.1 ± 2.1 | 20.3 ± 4.1 | 26.7 ± 5.7 | 34.7 ± 4.3 |
| Example 5 | 0.0 ± 0.0 | 12.1 ± 2.8 | 17.6 ± 4.2 | 23.6 ± 3.9 | 30.6 ± 4.8 | 37.2 ± 5.0 |
| Furozin solution | 0.0 ± 0.0 | 0.0 ± 0.0 | 0.0 ± 0.0 | 0.4 ± 0.3 | 1.2 ± 0.9 | 7.5 ± 3.6 |
| 70% Ethanol | 0.0 ± 0.0 | 0.0 ± 0.0 | 0.0 ± 0.0 | 0.5 ± 0.5 | 1.5 ± 1.5 | 8.0 ± 3.26 |

| | Hair regrowing rate (%) | | | | | |
|---|---|---|---|---|---|---|
| | 16 days | 18 days | 20 days | 22 days | 25 days | 28 days |
| Comparative Example 1 | 28.5 ± 3.7 | 41.7 ± 8.9 | 64.5 ± 11.5 | 77.3 ± 14.3 | 90.4 ± 18.9 | 100.0 ± 0.0 |
| Comparative Example 2 | 15.2 ± 5.2 | 40.6 ± 9.5 | 54.7 ± 14.2 | 72.5 ± 14.5 | 85.6 ± 15.2 | 97.4 ± 2.1 |
| Example 1 | 35.2 ± 4.2 | 50.0 ± 10.7 | 75.1 ± 12.5 | 88.5 ± 16.5 | 95.2 ± 14.6 | 98.0 ± 1.8 |
| Example 2 | 33.6 ± 4.8 | 48.2 ± 9.9 | 73.1 ± 11.6 | 87.7 ± 17.5 | 93.1 ± 3.2 | 97.6 ± 2.1 |
| Comparative Example 3 | 16.4 ± 6.3 | 46.4 ± 10.6 | 74.6 ± 12.8 | 85.4 ± 16.5 | 89.1 ± 7.7 | 96.3 ± 3.5 |
| Example 3 | 37.2 ± 5.0 | 36.1 ± 7.7 | 51.2 ± 11.2 | 75.3 ± 14.4 | 86.6 ± 14.4 | 98.0 ± 1.8 |
| Example 4 | 34.7 ± 4.3 | 45.2 ± 8.8 | 66.6 ± 12.3 | 80.3 ± 13.5 | 93.2 ± 7.5 | 100.0 ± 0.0 |
| Example 5 | 37.2 ± 5.0 | 52.2 ± 11.2 | 74.1 ± 11.5 | 89.0 ± 16.6 | 96.2 ± 4.0 | 100.0 ± 0.0 |
| Furozin solution | 7.5 ± 3.6 | 17.3 ± 7.3 | 30.5 ± 10.0 | 50.6 ± 16.7 | 70.4 ± 18.3 | 84.2 ± 11.9 |
| 70% Ethanol | 8.0 ± 3.2 | 16.8 ± 8.4 | 29.9 ± 15.7 | 48.8 ± 19.9 | 68.5 ± 20.6 | 83.5 ± 13.2 |

EXPERIMENT EXAMPLE 2

184 patients suffering from alopicia of various types were divided into 10 groups in such a manner that the type and

TABLE 3

|  | 1 | 2 | Example 1 | Example 2 | 5 | Example 3 | Example 4 | Example 5 | Furozin solution | 70% Ethanol |
|---|---|---|---|---|---|---|---|---|---|---|
| Fresh and terminal hair is recognized | 2 | 4 | 2 | 3 | 3 | 5 | 6 | 9 | 0 case | 0 case |
| Fresh and vellus hair is recognized | 9 | 10 | 6 | 5 | 8 | 10 | 8 | 8 | 6 cases | 3 cases |
| Reduction in falling out of hair is recognized | 6 | 3 | 1 | 2 | 8 | 2 | 3 | 4 | 3 cases | 3 cases |
| No change is recognized at all | 4 | 2 | 1 | 1 | 3 | 2 | 3 | 2 | 10 cases | 14 cases |
| Total | 21 | 19 | 10 | 11 | 22 | 19 | 20 | 23 | 19 cases | 20 cases |

It is apparent from the results given in Table 3 that a higher rate of improvement was obtained when the mulberry bark extract, persimmon leaf extract, paulownia leaf extract or the mixture of these extracts was used as compared with that obtained when the control (furozin solution or 70% ethanol solution) was used. It was also found that the mixture of the extracts exhibits a more excellent effect than that obtained by using the extract singly. Particularly, the mixture of three extracts from mulberry bark, persimmon leaves and paulownia leaves has an excellent effect. In the course of the test, no side effect supposedly caused by the sample was recognized in any group.

The hair growth promoter of the present invention has an effect of accelerating the proliferation of the human hair follicle cells which constitute the human hair follicle and which form the hair and also an effect of accelerating the hair growth in mice. When the hair growth promoter is applied to the human beings, excellent effects of preventing the hair from falling out and accelerating the hair growth are obtained.

Thus, the hair growth promoter of the present invention is effectively usable for the treatment or prevention of an alopecia such as premature alopecia or alopecia diffuse.

What is claimed is:

1. A hair growth promoter composition for treating premature alopecia and alopecia diffuse comprising, as an active ingredient, an extract obtained by extraction from a mixture of (i) mulberry bark comprising mulberry root bark of Morus bombycis Koidzumi, mulberry root bark of Morus alba Linne or mulberry root bark of a plant of the same genus thereof and (ii) leaves of persimmon (Diospyros Kaki Thunb), with an extracting solvent, wherein each of the mulberry root bark and the persimmon is in an amount of 0.001 to 20% by weight, based on the hair growth promoter composition, wherein the mixture is in an effective amount such that when the hair growth promoter is applied to one's scalp, fresh and vellus hair is recognized or a reduction of falling out of hair is recognized.

2. A hair growth promoter composition for treating premature alopecia and alopecia diffuse comprising, as an active ingredient, a mixture of (i) an extract obtained by extraction from mulberry bark comprising mulberry root bark of Morus bombycis Koidzumi, mulberry root bark of Morus alba Linne, or mulberry root bark of a plant of the same genus thereof, with an extracting solvent and (ii) an extract obtained by extraction from leaves of persimmon (Diospyros Kaki Thunb), with an extracting solvent, wherein each of the mulberry root bark and the persimmon is in an amount of 0.001 to 20% by weight, based on the hair growth promoter composition, wherein the mixture is in an effective amount such that when the hair growth promoter is applied to one's scalp, fresh and vellus hair is recognized or a reduction of falling out of hair is recognized.

3. A hair growth promoter composition for treating premature alopecia and alopecia diffuse comprising, as an active ingredient, an effective hair growth promoter amount of a mixture of (i) an extract obtained by extraction from a mixture of (a) mulberry bark comprising mulberry root bark of Morus bombycis Koidzumi, mulberry root bark of Morus alba Linne, or mulberry root bark of a plant of the same genus thereof and (b) leaves of persimmon (Diospyros Kaki Thunb), with an extracting solvent and (ii) an extract obtained by extraction from leaves of paulownia (Paulowinia tomantosa Steud.) with an extracting solvent, wherein each of the mulberry bark, the persimmon and the paulownia is in an amount of 0.001 to 20% by weight, based on the hair growth promoter composition, wherein the mixture is in an effective amount such that when the hair growth promoter is applied to one's scalp, fresh and vellus hair is recognized or a reduction of falling out of hair is recognized.

4. A hair growth promoter composition for treating premature alopecia and alopecia diffuse comprising, as an active ingredient, a mixture of (i) an extract obtained by extraction from mulberry bark comprising mulberry root bark of Morus bombycis Koidzumi, mulberry root bark of Morus alba Linne, or mulberry root bark of a plant of the same genus thereof, with an extracting solvent, (ii) an extract obtained by extraction from leaves of persimmon (Diospyros Kaki Thunb), with an extracting solvent and (iii) an extract obtained by extraction from leaves of paulownia (Paulowinia tomantosa Steud.), with an extracting solvent, wherein each of the mulberry bark, the persimmon and the paulownia is in an amount of 0.001 to 20% by weight, based on the hair growth promoter composition, wherein the mixture is in an effective amount such that when the hair growth promoter is applied to one's scalp, fresh and vellus hair is recognized or a reduction of falling out of hair is recognized.

5. A hair growth promoter composition for treating premature alopecia and alopecia diffuse comprising as an active ingredient, a mixture of (i) an extract obtained by extraction from mulberry bark comprising mulberry root bark of Morus bombycis Koidzumi, mulberry root bark of Morus alba Linne, or mulberry root bark of a plant of the same genus thereof, with an extracting solvent and (ii) an extract obtained by extraction from leaves of paulownia (Paulowinia tomantosa Steud.), with an extracting solvent, wherein each of the mulberry bark and the paulownia is in an amount of 0.001 to 20% by weight, based on the hair growth promoter composition, wherein the mixture is in an effective amount such that when the hair growth promoter is applied to one's scalp, fresh and vellus hair is recognized or a reduction of falling out of hair is recognized.

6. A hair growth promoter composition for treating premature alopecia and alopecia diffuse comprising, as an active ingredient, a mixture of (i) an extract obtained by extraction from leaves of persimmon (Diospyros Kaki Thunb), with an extracting solvent and (ii) an extract obtained by extraction from leaves of paulownia (Paulowinia tomantosa Steud.), with an extracting solvent, wherein each of the persimmon and the paulownia is in an amount of 0.001 to 20% by weight based on the hair growth promoter composition, wherein the mixture is in an effective amount such that when the hair growth promoter is applied to one's scalp, fresh and vellus hair is recognized or a reduction of falling out of hair recognized.

7. The hair growth promoter of claim 1, wherein the mulberry bark is in an amount of 0.1 to 5% by weight and the persimmon is in an amount of 0.05 to 3% by weight.

8. The hair growth promoter of claim 2, wherein the mulberry bark is in an amount of 0.1 to 5% by weight and the persimmon is in an amount of 0.05 to 3% by weight.

9. The hair growth promoter of claim 3, wherein the mulberry bark is in an amount of 0.1 to 5% by weight, the persimmon is in an amount of 0.05 to 3% by weight and the paulownia is in an amount of 0.1 to 10% by weight.

10. The hair growth promoter of claim 4, wherein the mulberry bark is in an amount of 0.1 to 5% by weight, the persimmon is in an amount of 0.05 to 3% by weight and the paulownia is in an amount of 0.1 to 10% by weight.

11. The hair growth promoter of claim 5, wherein the mulberry bark is in an amount of 0.1 to 5% by weight and the paulownia is in an amount of 0.1 to 10% by weight.

12. The hair growth promoter of claim 6, wherein the persimmon is in an amount of 0.05 to 3% by weight and the paulownia is in an amount of 0.1 to 10% by weight.

13. A method of promoting hair growth for the treatment of premature alopecia or alopecia diffuse comprising applying to the scalp of a human in need thereof an effective hair growth promoter amount of a hair growth promoter of claim 1.

14. A method of promoting hair growth for the treatment of premature alopecia or alopecia diffuse comprising applying to the scalp of a human in need thereof an effective hair growth promoter amount of a hair growth promoter of claim 2.

15. A method of promoting hair growth for the treatment of premature alopecia or alopecia diffuse comprising applying to the scalp of a human in need thereof an effective hair growth promoter amount of a hair growth promoter of claim 3.

16. A method of promoting hair growth for treatment of premature alopecia or alopecia diffuse comprising applying to the scalp of a human in need thereof an effective hair growth promoter amount of a hair growth promoter of claim 4.

17. A method of promoting hair growth for the treatment of premature alopecia or alopecia diffuse comprising applying to the scalp of a human in need thereof an effective hair growth promoter amount of a hair growth promoter of claim 5.

18. The method of promoting hair growth for the treatment of premature alopecia or alopecia diffuse comprising applying to the scalp of a human in need thereof an effective hair growth promoter amount of a hair growth promoter of claim 6.

* * * * *